US011920143B2

(12) United States Patent
Shan et al.

(10) Patent No.: US 11,920,143 B2
(45) Date of Patent: Mar. 5, 2024

(54) **PLASMID COMBINATION, RECOMBINANT AGROBACTERIUM TUMEFACIENS, AND METHOD FOR IMPROVING *PHYTOPHTHORA* RESISTANCE OF PLANTS**

(71) Applicant: NORTHWEST A&F UNIVERSITY, Xianyang (CN)

(72) Inventors: Weixing Shan, Xianyang (CN); Yang Yang, Xianyang (CN)

(73) Assignee: NORTHWEST A&F UNIVERSITY, Xianyang (CN)

( * ) Notice: Subject to any disclaimer, the term of this patent is extended or adjusted under 35 U.S.C. 154(b) by 79 days.

(21) Appl. No.: 17/214,636

(22) Filed: Mar. 26, 2021

(65) Prior Publication Data

US 2021/0301299 A1 Sep. 30, 2021

(30) Foreign Application Priority Data

Mar. 30, 2020 (CN) ......................... 202010237638.2

(51) Int. Cl.
*C12N 15/82* (2006.01)
*C12R 1/41* (2006.01)

(52) U.S. Cl.
CPC ...... *C12N 15/8282* (2013.01); *C12N 15/8205* (2013.01); *C12N 15/8279* (2013.01); *C12R 2001/41* (2021.05)

(58) Field of Classification Search
None
See application file for complete search history.

(56) References Cited

U.S. PATENT DOCUMENTS

2015/0203865 A1* 7/2015 Jin .................... C12N 15/8282 800/301

OTHER PUBLICATIONS

Friedberg (Automated protein function prediction—the genomic challenge. Brief. Bioinformatics. 7:225-242, 2006) (Year: 2006).*
Laluk et al (The *Arabidopsis* Mitochondria-Localized Pentatricopeptide Repeat Protein PGN Functions in Defense against Necrotrophic Fungi and Abiotic Stress Tolerance. Plant Physiology, vol. 156, pp. 2053-2068, Aug. 2011) (Year: 2011).*
Ye et al (Filamentous pathogen effectors interfering with small RNA silencing in plant hosts. Current Opinion in Microbiology, 32:1-6, 2016) (Year: 2016).*
Cheng et al (Araport11: a complete reannotation of the *Arabidopsis thaliana* reference genome. The Plant Journal 89, 789-804, 2017) (Year: 2017).*
The Potato Genome Sequencing Consortium (Genome sequence and analysis of the tuber crop potato. Nature 475:189-195, 2011). (Year: 2011).*
Faivre-Rampant et al (Potato Virus X-Induced Gene Silencing in Leaves and Tubers of Potato. Plant Physiology, Apr. 2004, vol. 134, pp. 1308-1316, 2004). (Year: 2004).*
Barkan et al (PentatricopeptideRepeat Proteins in Plants. Annu. Rev. Plant Biol. 65:415-442, 2014), most plant species have more than 400 members of PentatricopeptideRepeat Proteins. (Year: 2014).*

* cited by examiner

*Primary Examiner* — Charles Logsdon
*Assistant Examiner* — Wayne Zhong
(74) *Attorney, Agent, or Firm* — MH2 TECHNOLOGY LAW GROUP, LLP

(57) ABSTRACT

The present disclosure discloses an AtPPR1 gene (negative regulatory factor) for *Phytophthora* resistance and homologous genes thereof, involving an AtPPR1 gene and a protein encoded by the AtPPR1 gene. The AtPPR1 gene has a nucleotide sequence of SEQ ID NO:6, and the protein encoded by the AtPPR1 gene has an amino acid sequence of SEQ ID NO:7. A function of the AtPPR1 gene of the present disclosure to improve *Phytophthora* resistance of plants can be used for the selective breeding of *Phytophthora*-resistant varieties. As a new type of negative immunoregulatory factor in plants, AtPPR1 negatively regulates the resistance of plants to *Phytophthora* by interfering with downstream signal transduction of endogenous jasmonic acid (JA) and salicylic acid (SA) and ROS signals in plants.

5 Claims, 4 Drawing Sheets

Specification includes a Sequence Listing.

SEQUENCE LISTING

<160> NUMBER OF SEQ ID NOS: 10

<210> SEQ ID NO 1
<211> LENGTH: 321
<212> TYPE: DNA
<213> ORGANISM: Artificial sequence
<220> FEATURE:
<223> OTHER INFORMATION: NbPPR1-specific fragment

<400> SEQUENCE: 1
agctgaggct ttgatggaaa aaatgtccga atgtggtttc ttgaaatgcc ctcttcctta 60
taatcacatg ctatccttat acatatccca agggcaacta gagaaggttc cccgcctgat 120
tcaggaattg aagaaaaata gctctcctga tattgtcaca tacaacctgg agttggcagt 180
ttgtgcatcc cagaatgatg ttgaagctgc agagaaaaca ttcgttgagc taaagaaggc 240
aaaattggat cctgattgga taacgtttag cacattaaca aacatctata ttaaaagctc 300
acttcaggat aaagcaaagt c 321

<210> SEQ ID NO 2
<211> LENGTH: 34
<212> TYPE: DNA
<213> ORGANISM: Artificial Sequence
<220> FEATURE:
<223> OTHER INFORMATION: AtPPR1-F

<400> SEQUENCE: 2
ccgctcgaga tgaataaaaa catgttggtt cgct 34

<210> SEQ ID NO 3
<211> LENGTH: 33
<212> TYPE: DNA
<213> ORGANISM: Artificial Sequence
<220> FEATURE:
<223> OTHER INFORMATION: AtPPR1-R

<400> SEQUENCE: 3
gctctagact aagaaatggt ggacgagatt tca 33

<210> SEQ ID NO 4
<211> LENGTH: 24
<212> TYPE: DNA
<213> ORGANISM: Artificial Sequence
<220> FEATURE:
<223> OTHER INFORMATION: qAtPPR1-F

<400> SEQUENCE: 4
aaaatgaatg atgcggagta tctc 24

<210> SEQ ID NO 5
<211> LENGTH: 23
<212> TYPE: DNA
<213> ORGANISM: Artificial Sequence
<220> FEATURE:
<223> OTHER INFORMATION: qAtPPR1-R

<400> SEQUENCE: 5
tagaatagct cgggtttatc cct 23

<210> SEQ ID NO 6
<211> LENGTH: 2165
<212> TYPE: DNA
<213> ORGANISM: Artificial Sequence
<220> FEATURE:
<223> OTHER INFORMATION: AtPPR1 gene -continued

<400> SEQUENCE: 6

```
attactcaaa cagcagagag agagagagag ctcagtaaac taaacaaaaa tgaataaaaa     60
catgttggtt cgctctgccc ggccaaccct agcctccatt caccgccttt tctccgccgc    120
cgccgccgcg actgtggaca cggcgacggc acccgtggtg aagcctcgca gcggaggagg    180
aaaaggagga gaatcggcca acaaaaaaga aacggtagtt ggaggaagag acactctagg    240
agggagatta ctaagccttg tgtatacgaa acgcagcgcc gttgttacta tccgtaaatg    300
gaaagaagaa ggccattccg ttcgcaaata cgaacttaat cgtatcgtta gagagcttcg    360
taagatcaaa cgctataaac acgctcttga ggttcgtgaa atttctctca attttgaatt    420
cgattgtgaa aactctgcga agtggtaaaa tgtttttttt tttgtgtgtg tgtgtagata    480
tgtgaatgga tggttgtaca ggaagatata aagctacaag caggtgatta tgctgtacat    540
ttggatttga tatctaaaat ccgtggttta aacagtgctg agaagttttt cgaagatatg    600
ccagatcaaa tgagaggtca tgctgcgtgt acatctcttt tacatagcta tgtgcagaac    660
aagttgtctg ataaagctga ggcattgttt gagaaaatgg gtgaatgtgg tttcttgaag    720
tcttgtttgc cttacaatca tatgttatcg atgtatatat cgagaggaca gtttgagaaa    780
gtccctgtgt tgattaagga gttgaagatt agaacatctc ctgatattgt tacttataat    840
ctctggctta ctgcgtttgc ttctggaaat gatgtcgagg gtgcggagaa agtttatctt    900
aaggcgaagg aagagaagtt gaatccggat tgggtgactt atagtgtgtt aacgaatttg    960
tatgctaaga ctgataatgt cgaaaaggcg agacttgctt tgaaggagat ggagaagttg   1020
gtttctaaga agaaccgggt tgcttatgct tctcttatta gtctgcatgc gaatttgggt   1080
gacaaagatg gagtgaactt aacctggaag aaggttaagt cttctttcaa gaaaatgaat   1140
gatgcggagt atctcagtat gatatctgcg gttgtgaagc ttggagagtt tgaacaagct   1200
aaaggtttgt atgacgaatg ggaatctgtt tcgggaacag gagatgctag aatcccgaat   1260
ctaatccttg ctgagtacat gaacagagat gaggttcttc taggagaaaa gttttacgaa   1320
cggattgtgg agaaagggat aaacccgagc tattctacat gggaaattct cacatgggct   1380
tatttgaagc gtaaagacat ggagaaagta ttagattgtt ttgggaaagc tattgattct   1440
gtgaagaaat ggactgtgaa tgtaagattg gttaaaggag cgtgcaagga acttgaggaa   1500
caagggaatg ttaaaggagc agagaagcta atgactctgc tccaaaaggc tggttatgtg   1560
aacactcagc tctacaattc cttgttacgg acatacgcta aagcagggga aatggcactc   1620
atagttgaag agcgaatggc aaaggataat gtagagttag atgaagagac taaggagctt   1680
ataagactaa ccagtcaaat gcgtgtgact gaaatctcgt ccaccatttc ttagtatgaa   1740
agctacagag ttagtttcag tctgcaactt ccacaaaccg aagaatacag aaaccgttct   1800
ctcaagtccg taccaatcga gatactcgtc ttgaagcagt aacattccac ttactcggac   1860
atttagacct tgaggagagt gttcaaagct gctaaggaat gaagttgcta caaagatatg   1920
atttttcctg ttttttaatt ttcagaattt aatatgatta aaatctcgtt ttatattttt   1980
ggttctctat agttcttctg atgatgtcaa atgatctttg agaggttgac taactgaaaa   2040
acctacttcg actcttcttg ttgggtagtt atgacttgtg taagcttatg taagctttca   2100
aagacttgtg tccaaagtgg atttgttcac ctccaaacac ttagtcaact attttaacca   2160
taaac                                                               2165
```

<210> SEQ ID NO 7

-continued

<211> LENGTH: 532
<212> TYPE: PRT
<213> ORGANISM: Artificial Sequence
<220> FEATURE:
<223> OTHER INFORMATION: AtPPR1(protein encoded by the AtPPR1 gene)

<400> SEQUENCE: 7

```
Met Asn Lys Asn Met Leu Val Arg Ser Ala Arg Pro Thr Leu Ala Ser
1               5                   10                  15

Ile His Arg Leu Phe Ser Ala Ala Ala Ala Ala Thr Val Asp Thr Ala
            20                  25                  30

Thr Ala Pro Val Val Lys Pro Arg Ser Gly Gly Gly Lys Gly Gly Glu
        35                  40                  45

Ser Ala Asn Lys Lys Glu Thr Val Val Gly Gly Arg Asp Thr Leu Gly
    50                  55                  60

Gly Arg Leu Leu Ser Leu Val Tyr Thr Lys Arg Ser Ala Val Val Thr
65                  70                  75                  80

Ile Arg Lys Trp Lys Glu Glu Gly His Ser Val Arg Lys Tyr Glu Leu
                85                  90                  95

Asn Arg Ile Val Arg Glu Leu Arg Lys Ile Lys Arg Tyr Lys His Ala
            100                 105                 110

Leu Glu Ile Cys Glu Trp Met Val Val Gln Glu Asp Ile Lys Leu Gln
        115                 120                 125

Ala Gly Asp Tyr Ala Val His Leu Asp Leu Ile Ser Lys Ile Arg Gly
    130                 135                 140

Leu Asn Ser Ala Glu Lys Phe Phe Glu Asp Met Pro Asp Gln Met Arg
145                 150                 155                 160

Gly His Ala Ala Cys Thr Ser Leu Leu His Ser Tyr Val Gln Asn Lys
                165                 170                 175

Leu Ser Asp Lys Ala Glu Ala Leu Phe Glu Lys Met Gly Glu Cys Gly
            180                 185                 190

Phe Leu Lys Ser Cys Leu Pro Tyr Asn His Met Leu Ser Met Tyr Ile
        195                 200                 205

Ser Arg Gly Gln Phe Glu Lys Val Pro Val Leu Ile Lys Glu Leu Lys
    210                 215                 220

Ile Arg Thr Ser Pro Asp Ile Val Thr Tyr Asn Leu Trp Leu Thr Ala
225                 230                 235                 240

Phe Ala Ser Gly Asn Asp Val Glu Gly Ala Glu Lys Val Tyr Leu Lys
                245                 250                 255

Ala Lys Glu Glu Lys Leu Asn Pro Asp Trp Val Thr Tyr Ser Val Leu
            260                 265                 270

Thr Asn Leu Tyr Ala Lys Thr Asp Asn Val Glu Lys Ala Arg Leu Ala
        275                 280                 285

Leu Lys Glu Met Glu Lys Leu Val Ser Lys Lys Asn Arg Val Ala Tyr
    290                 295                 300

Ala Ser Leu Ile Ser Leu His Ala Asn Leu Gly Asp Lys Asp Gly Val
305                 310                 315                 320

Asn Leu Thr Trp Lys Lys Val Lys Ser Ser Phe Lys Lys Met Asn Asp
                325                 330                 335

Ala Glu Tyr Leu Ser Met Ile Ser Ala Val Val Lys Leu Gly Glu Phe
            340                 345                 350

Glu Gln Ala Lys Gly Leu Tyr Asp Glu Trp Glu Ser Val Ser Gly Thr
        355                 360                 365

Gly Asp Ala Arg Ile Pro Asn Leu Ile Leu Ala Glu Tyr Met Asn Arg
    370                 375                 380
```

-continued

```
Asp Glu Val Leu Leu Gly Glu Lys Phe Tyr Glu Arg Ile Val Glu Lys
385                 390                 395                 400

Gly Ile Asn Pro Ser Tyr Ser Thr Trp Glu Ile Leu Thr Trp Ala Tyr
                405                 410                 415

Leu Lys Arg Lys Asp Met Glu Lys Val Leu Asp Cys Phe Gly Lys Ala
            420                 425                 430

Ile Asp Ser Val Lys Lys Trp Thr Val Asn Val Arg Leu Val Lys Gly
        435                 440                 445

Ala Cys Lys Glu Leu Glu Glu Gln Gly Asn Val Lys Gly Ala Glu Lys
    450                 455                 460

Leu Met Thr Leu Leu Gln Lys Ala Gly Tyr Val Asn Thr Gln Leu Tyr
465                 470                 475                 480

Asn Ser Leu Leu Arg Thr Tyr Ala Lys Ala Gly Glu Met Ala Leu Ile
                485                 490                 495

Val Glu Glu Arg Met Ala Lys Asp Asn Val Glu Leu Asp Glu Glu Thr
            500                 505                 510

Lys Glu Leu Ile Arg Leu Thr Ser Gln Met Arg Val Thr Glu Ile Ser
        515                 520                 525

Ser Thr Ile Ser
    530


<210> SEQ ID NO 8
<211> LENGTH: 454
<212> TYPE: PRT
<213> ORGANISM: Artificial Sequence
<220> FEATURE:
<223> OTHER INFORMATION: StPPR1-1 (XP_015167864.1)

<400> SEQUENCE: 8

Ile Ala Ile Ser Lys Trp Lys Glu Glu Gly Arg Pro Val Arg Lys Tyr
1               5                   10                  15

Glu Leu Asn Arg Ile Val Gln Glu Leu Arg Lys His Lys Arg Tyr Lys
            20                  25                  30

His Ala Leu Glu Val Cys Glu Trp Met Arg Val Gln Asp Asp Ile Gln
        35                  40                  45

Leu Leu Tyr Gly Asp Tyr Ala Val His Leu Asp Leu Ile Ala Lys Val
    50                  55                  60

Arg Cys Met Asn Ser Ala Lys Lys Phe Phe Glu Asp Leu Pro Asp Lys
65                  70                  75                  80

Leu Lys Val Gln Thr Thr Cys Thr Ala Leu Leu His Thr Tyr Val Gln
                85                  90                  95

His Lys Asn Ile Ala Lys Ala Glu Ser Leu Met Lys Lys Met Ser Glu
            100                 105                 110

Cys Gly Phe Leu Asn Tyr His Leu Pro Tyr Asn His Met Leu Thr Leu
        115                 120                 125

Tyr Ile Ser Gln Gly Gln Leu Glu Lys Val Leu Gly Leu Ile Gln Glu
    130                 135                 140

Leu Lys Lys Asn Thr Ser Pro Asp Ile Val Thr Tyr Asn Leu Glu Leu
145                 150                 155                 160

Ala Val Phe Ala Ser Gln Asn Asn Val Glu Ala Ala Glu Lys Met Leu
                165                 170                 175

Leu Glu Leu Lys Lys Ala Lys Leu Asp Pro Asp Trp Ile Thr Phe Ser
            180                 185                 190

Thr Leu Thr Asn Ile Tyr Ile Lys Ser Ser Leu Gln Asp Lys Ala Asn
        195                 200                 205
```

Ser Thr Leu Gln Glu Met Glu Lys Lys Ile Ser Arg Lys Ala Arg Thr
    210                 215                 220

Ala Tyr Val Ser Leu Ile Ser Leu His Thr Asn Leu Gln Asn Lys Asp
225                 230                 235                 240

Glu Val Phe Arg Ile Trp Lys Glu Met Lys Ser Ile Phe Arg Lys Val
                245                 250                 255

Asn Asp Thr Glu Tyr Ser Cys Ile Ile Ser Leu Leu Leu Lys Leu Asp
            260                 265                 270

Glu Phe Gly Glu Ala Met Asn Leu Tyr Thr Glu Trp Glu Ala Val Ser
        275                 280                 285

Val Thr Lys Asp Thr Arg Ile Ala Asn Leu Ile Leu Ala Ala Tyr Ile
    290                 295                 300

Asn Lys Asn Glu Met Glu Lys Ala Val Asn Phe His Asn Lys Met Met
305                 310                 315                 320

Gln Lys Gly Ile Ser Pro Ser Cys Thr Thr Trp Glu Leu Leu Thr Arg
                325                 330                 335

Gly Tyr Leu Lys Gln Lys Glu Met Asp Lys Val Leu Glu Val Phe Lys
            340                 345                 350

Lys Thr Val Thr Ser Val Ser Lys Trp Asp Pro Asp Ala Lys Met Val
        355                 360                 365

Arg Glu Met Tyr His Val Val Glu Glu Gln Gly Asp Ile Gln Val Ala
    370                 375                 380

Glu Gln Leu Leu Val Thr Leu Arg His Ala Lys Tyr Val Asn Thr Glu
385                 390                 395                 400

Ile Tyr Asn Ala Leu Leu Arg Thr Tyr Val Asn Ala Gly Lys Met Pro
                405                 410                 415

Met Ile Val Glu Glu Arg Met Lys Lys Asp Asn Val Glu Met Asp Glu
            420                 425                 430

Glu Thr Gln Lys Leu Ile Gly Ile Thr Ser Lys Met Thr Val Thr Glu
        435                 440                 445

Val Pro Asn Glu Ile Ala
    450

<210> SEQ ID NO 9
<211> LENGTH: 524
<212> TYPE: PRT
<213> ORGANISM: Artificial Sequence
<220> FEATURE:
<223> OTHER INFORMATION: StPPR1-2 (XP_006366127.1)

<400> SEQUENCE: 9

Met Leu Leu Arg Leu Ile Arg Arg Ser Tyr Ala Ala Val Arg Pro Leu
1               5                   10                  15

Ser Ile Glu Ala Ser Thr Thr Val Lys Ser Thr Arg Ser Gly Gly Gly
            20                  25                  30

Ser Ser Ile Thr Thr Ser Leu Glu Gly Gly Thr Ser Thr Ala Thr Ser
        35                  40                  45

Thr Arg Gly Arg Asp Thr Leu Gly Arg Arg Leu Leu Ser Leu Ile Tyr
    50                  55                  60

Ala Lys Arg Ser Ala Val Ile Ala Ile Arg Lys Trp Lys Glu Glu Gly
65                  70                  75                  80

His Pro Val Arg Lys Tyr Glu Leu Asn Arg Ile Val Arg Glu Leu Arg
                85                  90                  95

Arg His Lys Arg Phe Lys His Ala Leu Glu Val Cys Glu Trp Met Arg
            100                 105                 110

-continued

```
Val Gln Asp Asp Ile Glu Leu Leu Ser Gly Asp Tyr Ala Val His Leu
        115                 120                 125

Asp Leu Ile Ala Lys Val Arg Gly Met Asn Ser Ala Glu Lys Phe Phe
    130                 135                 140

Glu Asp Leu Pro Asp Lys Leu Lys Val Gln Thr Thr Cys Thr Ala Leu
145                 150                 155                 160

Leu His Thr Tyr Val Gln His Lys Asp Thr Ala Lys Ala Glu Ser Leu
                165                 170                 175

Met Glu Lys Met Ser Glu Cys Gly Phe Leu Lys Tyr Pro Leu Pro Tyr
            180                 185                 190

Asn His Met Leu Thr Leu Tyr Ile Ser Gln Gly Gln Leu Glu Lys Val
        195                 200                 205

Pro Gly Leu Ile Lys Glu Leu Lys Lys Asn Thr Ser Pro Asp Ile Val
    210                 215                 220

Thr Tyr Asn Leu Glu Leu Ala Val Phe Ala Ser Gln Asn Asn Val Glu
225                 230                 235                 240

Ala Ala Glu Lys Ala Phe Leu Glu Leu Lys Lys Ala Lys Leu Asp Pro
                245                 250                 255

Asp Trp Ile Thr Phe Ser Thr Leu Thr Asn Ile Tyr Ile Lys Ser Ser
            260                 265                 270

Leu Gln Asp Lys Ala Lys Ser Thr Leu Arg Glu Met Glu Lys Arg Ile
        275                 280                 285

Ser Arg Lys Gly Arg Thr Ala Tyr Ala Ser Leu Ile Ser Leu His Thr
    290                 295                 300

Asn Leu Gln Ser Lys Asp Glu Val Phe Arg Ile Trp Lys Glu Met Lys
305                 310                 315                 320

Ser Leu Phe Arg Lys Val Asn Asp Thr Glu Tyr Ser Cys Ile Ile Ser
                325                 330                 335

Ser Leu Leu Lys Leu Asp Glu Phe Gly Glu Ala Met Asn Leu Tyr Thr
            340                 345                 350

Glu Trp Glu Ala Gly Ser Val Thr Lys Asp Thr Arg Ile Ala Asn Leu
        355                 360                 365

Ile Leu Ala Ala Tyr Ile Asn Arg Ser Glu Met Glu Asn Ala Val Asp
    370                 375                 380

Phe His Asn Arg Met Ala Glu Lys Gly Ile Thr Pro Ser Cys Thr Thr
385                 390                 395                 400

Trp Lys Leu Leu Thr Gln Gly Tyr Leu Lys Gln Lys Glu Met Asp Lys
                405                 410                 415

Val Val Glu Phe Phe Lys Lys Thr Val Thr Ser Val Ser Lys Trp Asp
            420                 425                 430

Pro Asp Ala Lys Met Val Gln Glu Met Phe His Val Val Glu Glu Gln
        435                 440                 445

Gly Asp Ile Gln Met Ala Glu Gln Leu Leu Val Thr Leu Arg His Ala
    450                 455                 460

Lys Tyr Val Asn Thr Glu Ile Tyr Asn Ala Leu Leu Arg Thr Tyr Val
465                 470                 475                 480

Asn Ala Gly Lys Met Pro Met Ile Val Thr Glu Arg Met Lys Lys Asp
                485                 490                 495

Asn Val Glu Met Asp Glu Glu Thr Arg Lys Leu Ile Gly Ile Thr Ser
            500                 505                 510

Lys Met Thr Val Thr Glu Val Pro Asn Gly Val Ala
        515                 520
```

<210> SEQ ID NO 10
<211> LENGTH: 545
<212> TYPE: PRT
<213> ORGANISM: Artificial Sequence
<220> FEATURE:
<223> OTHER INFORMATION: NbPPR1 (Niben101Scf00317g06017.1)

<400> SEQUENCE: 10

```
Met Ser Arg Ser Leu Ser Val Leu Arg Leu Lys Met Leu Leu Arg Leu
1               5                   10                  15

Val Gln Arg Ser Phe Val Ala Val Arg Pro Leu Ser Thr Glu Ala Ala
            20                  25                  30

Thr Ala Val Lys Ser Thr Ser Leu Gly Gly Gly Thr Ser Ser Ser Thr
        35                  40                  45

Arg Leu Glu Gly Val Thr Ser Ile Thr Thr Ser Leu Lys Gly Gly Ser
    50                  55                  60

Ser Asn Thr Ile Ser Thr Ser Gly Arg Asp Thr Leu Gly Lys Arg Leu
65                  70                  75                  80

Leu Ser Leu Ile Tyr Ala Lys Arg Ser Ala Val Ile Ala Ile Arg Lys
                85                  90                  95

Trp Lys Glu Glu Gly His Pro Val Arg Lys Tyr Glu Leu Asn Arg Ile
            100                 105                 110

Val Arg Glu Leu Arg Arg His Lys Arg Tyr Lys His Ala Leu Glu Val
        115                 120                 125

Cys Glu Trp Met Arg Val Gln Asp Asp Ile Gln Leu Leu Pro Gly Asp
    130                 135                 140

Tyr Ala Val His Leu Asp Leu Ile Ala Lys Val Arg Gly Met Asn Ser
145                 150                 155                 160

Ala Glu Lys Phe Phe Glu Asp Leu Pro Asp Lys Leu Lys Ala Gln Thr
                165                 170                 175

Thr Cys Thr Ala Leu Leu His Asn Tyr Val Gln His Lys Asn Thr Ala
            180                 185                 190

Lys Ala Glu Ala Leu Met Glu Lys Met Ser Glu Cys Gly Phe Leu Lys
        195                 200                 205

Cys Pro Leu Pro Tyr Asn His Met Leu Ser Leu Tyr Ile Ser Gln Gly
    210                 215                 220

Gln Leu Glu Lys Val Pro Arg Leu Ile Gln Glu Leu Lys Lys Asn Ser
225                 230                 235                 240

Ser Pro Asp Ile Val Thr Tyr Asn Leu Glu Leu Ala Val Cys Ala Ser
                245                 250                 255

Gln Asn Asp Val Glu Ala Ala Glu Lys Thr Phe Val Glu Leu Lys Lys
            260                 265                 270

Ala Lys Leu Asp Pro Asp Trp Ile Thr Phe Ser Thr Leu Thr Asn Ile
        275                 280                 285

Tyr Ile Lys Ser Ser Leu Gln Asp Lys Ala Lys Ser Thr Leu Arg Glu
    290                 295                 300

Met Glu Lys Arg Ile Ser Arg Lys Val Arg Ala Ala Tyr Gly Ser Leu
305                 310                 315                 320

Leu Ser Leu His Thr Asn Leu Lys Ser Lys Asp Glu Val Leu Arg Ile
                325                 330                 335

Trp Lys Lys Met Lys Ser Thr Tyr Arg Lys Leu Asn Asp Ala Glu Tyr
            340                 345                 350

Thr Cys Met Ile Ser Ser Val Leu Lys Leu Asp Glu Phe Gly Glu Ala
        355                 360                 365
```

-continued

```
Met Asn Leu Tyr Thr Glu Trp Glu Ser Val Ser Val Thr Arg Asp Ser
    370                 375                 380

Arg Ile Ser Asn Leu Leu Leu Ala Ala Tyr Ile Asn Lys Asn Glu Met
385                 390                 395                 400

Glu Lys Ala Val Asp Phe His Asn Arg Met Val Gln Lys Gly Val Ser
                405                 410                 415

Pro Ser Tyr Thr Thr Trp Glu Leu Leu Thr Trp Gly Tyr Leu Lys Gln
            420                 425                 430

Lys Glu Met Gly Lys Val Leu Glu Phe Phe Lys Arg Ala Val Thr Ser
        435                 440                 445

Val Ser Lys Trp Asp Pro Asp Ala Lys Leu Val Gln Glu Met Phe His
    450                 455                 460

Val Val Glu Glu Gln Gly Asn Val Leu Val Ala Glu Gln Leu Leu Val
465                 470                 475                 480

Thr Leu Arg His Ala Lys Tyr Gly Asn Thr Glu Ile Tyr Asn Ala Leu
                485                 490                 495

Leu Arg Thr Tyr Ala Lys Ala Gly Lys Met Pro Met Ile Val Ala Glu
            500                 505                 510

Arg Met Lys Lys Asp Asn Val Lys Met Asp Glu Glu Thr Gln Lys Leu
        515                 520                 525

Ile Thr Leu Thr Ser Lys Met Thr Val Thr Glu Val Pro Ser Ser Ile
    530                 535                 540

Ala
545
```

PLASMID COMBINATION, RECOMBINANT AGROBACTERIUM TUMEFACIENS, AND METHOD FOR IMPROVING *PHYTOPHTHORA* RESISTANCE OF PLANTS

CROSS-REFERENCE TO RELATED APPLICATIONS

This application claims priority under 35 U.S.C. § 119 to Chinese Patent Application No. 202010237638.2, which was filed on 30 Mar. 2020, the contents of which are hereby expressly incorporated by reference in its entirety.

SEQUENCE LISTING

The instant application contains a Sequence Listing which has been submitted electronically in ASCII format and is hereby incorporated by reference in its entirety. Said ASCII copy, created on 24 Mar. 2021, is named SequenceListing.txt and is 23 kilobytes in size.

TECHNICAL FIELD

The present disclosure relates to the field of biotechnology, and in particular to a plasmid combination, a recombinant *Agrobacterium tumefaciens*, and a method for improving *Phytophthora* resistance of plants.

BACKGROUND

Oomycetes are a group of eukaryotic microorganisms that grow like fungal hyphae and include *Phytophthora*. Oomycetes are grouped with algae in evolution, but are an independent and uniquely-distributed population, including *Phytophthora*, Saprolegniales, Peronosporales, and so on. Many members of *Phytophthora* can cause destructive plant diseases. For example, potato late blight caused by *Phytophthora infestans* (*P. infestans*) resulted in the Great Irish Famine in the 19th century, which made the Irish population plummet by nearly a quarter and about one million people emigrate overseas due to hunger, and posed a profound impact on politics, economy, and culture of Ireland. Tobacco black shank caused by *Phytophthora parasitica* (*P. parasitica*) is one of the major tobacco diseases in the world, which occurs in various major tobacco-producing areas of China every year to varying degrees and poses a serious threat to the global tobacco industry.

At present, the prevention and control of oomycetes such as *Phytophthora* mainly relies on the use of existing disease-resistant varieties and chemical control methods. However, due to the rapid evolution of *Phytophthora, Phytophthora* easily mutates to make disease-resistant varieties lose resistance and tends to produce resistance to chemical agents. Therefore, it is imperative to develop new ways and tap new resources for fighting against the disease.

In a process of compatible interaction between plants and pathogens, pathogens rely on a series of processes such as nutrient transmission, molecular exchange, and hormone signal transduction that regulate by plant disease-related factors to achieve successful infection and colonization. If these disease-related factors are missing, plants will show resistance to pathogens, which provides new ideas for disease-resistance and breeding of plants. The strategy of finding natural mutants of plant disease-related factors or making plant disease-related factors lose functions through site-directed mutations to enhance the resistance of plants has been used in the breeding of fungus-resistant plants.

At present, many negative immunoregulatory factors for oomycete resistance of plants have been identified, most of which are for resistance to oomycetes of Peronosporales. There is less research on negative immunoregulatory factors for *Phytophthora* resistance, and specific active mechanisms of many negative immunoregulatory factors are still unclear. Although the use of negative immunoregulatory factors for oomycete resistance in potatoes has been explored in recent years, these negative immunoregulatory factors have not yet been used in the disease resistance and breeding of crops. Therefore, the present disclosure provides an AtPPR1 gene for *Phytophthora* resistance and homologous genes thereof to solve the deficiencies in the prior art.

SUMMARY

In view of the above-mentioned problems, the present disclosure provides an AtPPR1 gene for *Phytophthora* resistance and homologous genes thereof. A function of the AtPPR1 gene of the present disclosure to improve *Phytophthora* resistance of plants can be used for the selective breeding of *Phytophthora*-resistant varieties. As a new type of negative immunoregulatory factor in plants, AtPPR1 can negatively regulate the resistance of plants to *Phytophthora* by interfering with downstream signal transduction of endogenous jasmonic acid (JA) and salicylic acid (SA) and ROS signals in plants.

The present disclosure provides an AtPPR1 gene for *Phytophthora* resistance, involving an AtPPR1 gene and a protein encoded by the AtPPR1 gene. The AtPPR1 gene has a nucleotide sequence of SEQ ID NO. 6, and the protein encoded by the AtPPR1 gene has an amino acid sequence of SEQ ID NO. 7.

The AtPPR1 gene has a homologous gene of NbPPR1 in *Nicotiana benthamiana*; and two homologous genes of the AtPPR1 gene in a sequenced potato genome have amino acid sequences of SEQ ID NO. 8 and SEQ ID NO. 9.

As a further improvement, an amino acid sequence corresponding to the NbPPR1 is shown in SEQ ID NO. 10.

As a further improvement, the NbPPR1 and AtPPR1 protein sequences have a similarity of more than 50%, and the NbPPR1 and AtPPR1 genes show a similar negative regulation to *Phytophthora* resistance in plants.

As a further improvement, two homologous proteins encoded by the two homologous genes of the AtPPR1 gene in the sequenced potato genome have an amino acid sequence similarity >50% with the AtPPR1 protein.

The present disclosure also provides use of the AtPPR1 gene and the protein encoded by the AtPPR1 gene in the prevention and treatment of potato late blight and tobacco black shank.

The present disclosure also provides use of the AtPPR1 gene, the homologous gene thereof, and the protein encoded by the AtPPR1 gene in *Phytophthora* resistance of plants.

Beneficial effects of the present disclosure: A function of the AtPPR1 gene of the present disclosure to improve *Phytophthora* resistance of plants can be used for the selective breeding of *Phytophthora*-resistant varieties. As a new type of negative immunoregulatory factor in plants, AtPPR1 can negatively regulate the resistance of plants to *Phytophthora* by interfering with downstream signal transduction of endogenous JA and SA and ROS signals in plants.

DETAILED DESCRIPTION

In order to deepen the understanding of the present disclosure, the present disclosure will be described in further detail below in conjunction with examples, but these examples are only used to explain the present disclosure and do not constitute a limitation on the protection scope of the present disclosure.

Example 1

This example provided the cloning of the AtPPR1 gene in *Arabidopsis thaliana*, including the following steps:

Step 1: Preparation of plant materials: wild-type *Arabidopsis thaliana* Col-0 was prepared (available through public channels). Extraction of RNA: RNA was extracted with an RNA extraction kit (OMGA, Lot #: R6827-01), the integrity of RNA was identified by agarose gel electrophoresis, and the purity and concentration of RNA were then determined on a spectrophotometer.

Step 2: Gene cloning: A reverse transcription kit (TaKaRa, Lot #: AHE3187A) was used to obtain cDNA of Col-0. The upstream and downstream primers AtPPR1-F/R were designed according to a full-length coding sequence of AtPPR1 (At4G02820) provided in the *Arabidopsis* Information Resource (TAIR) website, and the cDNA was used as a template for amplification. PCR products were subjected to enzyme digestion, ligation, and bacterial liquid PCR verification and then used to construct vectors pKannibal-AtPPR1, which were sent for sequencing. Sequencing results were aligned with a published sequence, and correct plasmids were used for subsequent experiments.

Primer Sequences:

AtPPR1-F: CCGCTCGAGATGAATAAAAA-CATGTTGGTTCGCT, shown in SEQ ID NO. 2; and

AtPPR1-R: GCTCTA-GACTAAGAAATGGTGGACGAGATTTCA, shown in SEQ ID NO. 3.

Example 2

This example provided the sequence information and homology analysis for the *Arabidopsis thaliana* AtPPR1 gene. A full-length CDS sequence of the *Arabidopsis thaliana* AtPPR1 gene was 1,599 bp, and a detailed sequence could be seen in SEQ ID NO: 6. An amino acid sequence of the gene had a total of 532 amino acids, and a detailed sequence could be seen in SEQ ID NO: 7.

The amino acid sequence of the protein encoded by the *Arabidopsis thaliana* AtPPR1 gene was subjected to homology search with the BLAST program, and results showed that one homologous gene NbPPR1 was found in *Nicotiana benthamiana*. Moreover, two homologous genes for AtPPR1 were also found in research of a potato genome. With an amino acid sequence similarity of more than 50%, the 3 homologous genes were inferred to have the same function as AtPPR1.

Figure 1:
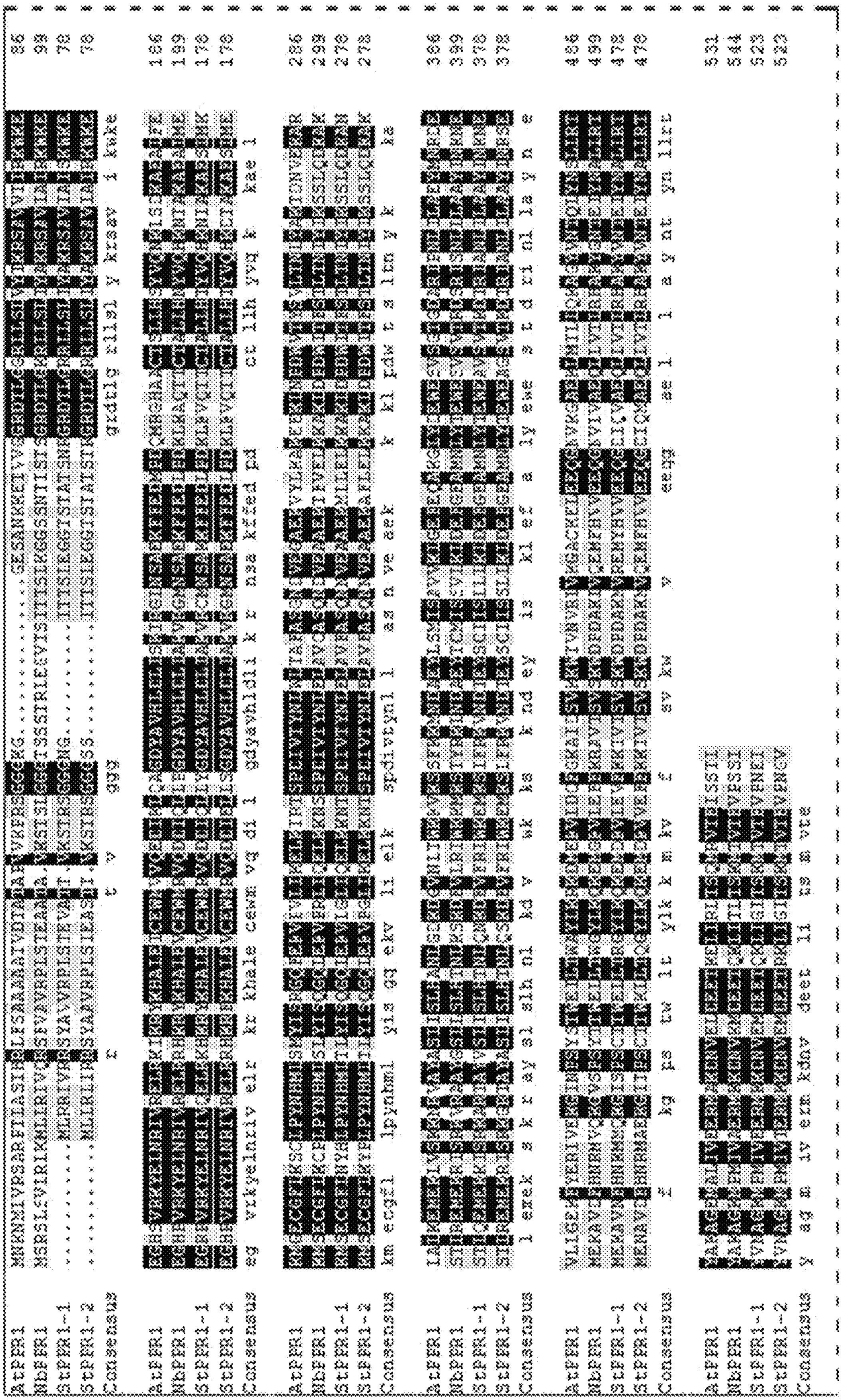
FIG. 1 is a schematic diagram illustrating the protein sequence alignment of AtPPR1 (SEQ ID NO. 7) with NbPPR1 (SEQ ID NO. 10), StPPR1-1 (SEQ ID NO. 8), and StPPR1-2 (SEQ ID NO. 9) according to Example 2 of the present disclosure.

FIG. 1 shows the alignment results of an amino acid sequence encoded by the *Arabidopsis thaliana* AtPPR1 gene with the amino acid sequences encoded by the three homologous genes in *Nicotiana benthamiana* and potato.

Example 3

This example showed that a T-DNA-inserted mutant of AtPPR1 *Arabidopsis thaliana* (purchased from *Arabidopsis* Biological Resource Center (ABRC)) exhibited the resistance to *P. parasitica, P. capsici*, and *P. syringae*, specifically including the following steps:

Step 1: Specific primers (qAtPPR1-F: AAAATGAAT-GATGCGGAGTATCTC, shown in SEQ ID NO. 4; and qAtPPR1-R: TAGAATAGCTCGGGTTTATCCCT, shown in SEQ ID NO. 5) were first designed to detect the expression of AtPPR1 in the mutant.

Step 2: About 0.1 g of an *Arabidopsis thaliana* sample was collected to extract RNA, which was reverse-transcribed into cDNA; then specific primers were designed; and the expression of AtPPR1 was detected using the real-time fluorescent quantitative PCR technology.

Step 3: AtPPR1 mutant *Arabidopsis thaliana* leaves at a seedling age of 4 to 5 weeks were collected, and wild-type *Arabidopsis thaliana* Col-0 was adopted as a control. The leaves were scratched and inoculated with about 2,000 GFP-labeled zoospores of *P. parasitica*, and then cultivated in a 23° C. incubator in the dark for about 48 h. Fluorescence observation and disease degree evaluation were conducted.

Step 4: *P. capsici* was inoculated at a zoospore number adjusted to about 800 and cultivated under conditions similar to that of *P. parasitica*. About 40 h after cultivation, a lesion diameter was observed and measured.

Step 5: A stored Pst DC3000 bacterial glycerol stock was streaked on an LB plate with corresponding antibiotics for activation, and then cultivated overnight at 28° C. in the dark.

Step 6: Single colonies were picked and inoculated into 3 mL of LB liquid medium with antibiotics, and cultivated at 28° C. with 220 rpm until $OD_{600}$=1; then bacteria were collected and resuspended in $dH_2O$, and $OD_{600}$ was adjusted to 0.1; the resulting solution was diluted 1,000 times and then injected into *Arabidopsis thaliana* leaves; and after the injection and three days after the inoculation, samples were collected at the same amount, then ground, and coated to analyze the reproduction of *P. syringae*.

Figure 2:
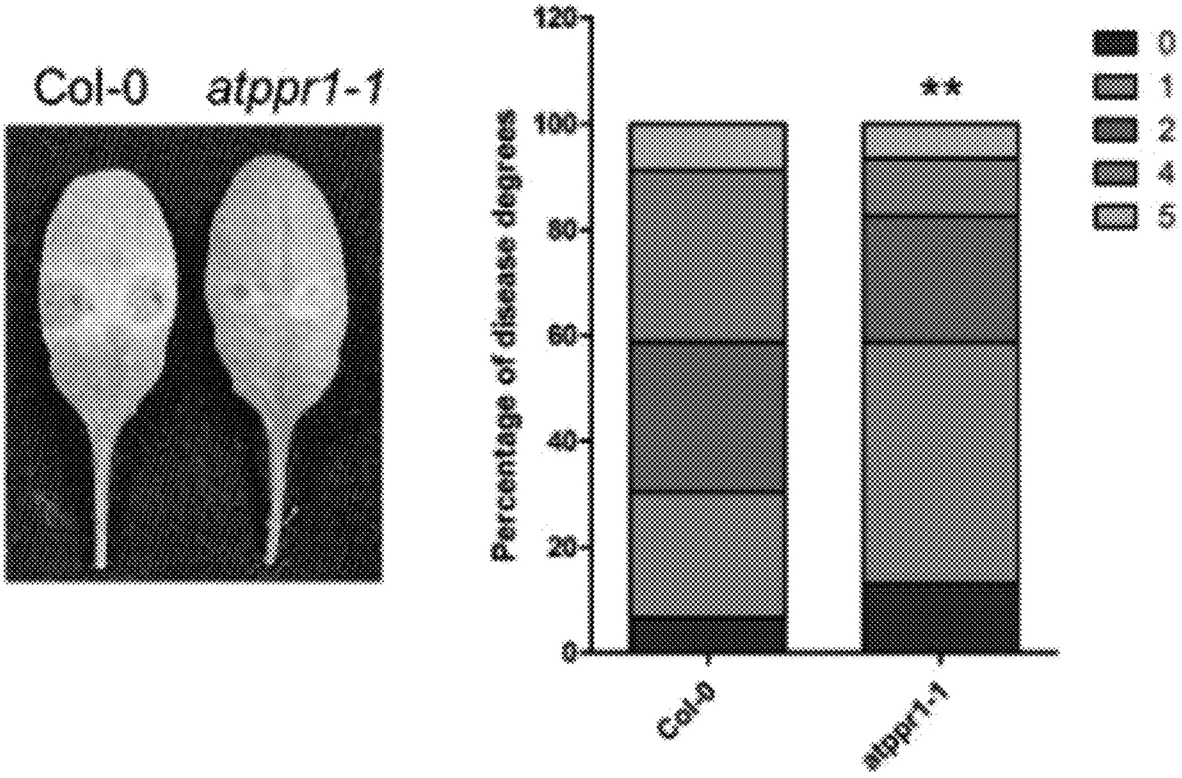
FIG. 2 is a schematic diagram illustrating the resistance of an AtPPR1-knockout mutant of *Arabidopsis thaliana* to *P. parasitica* according to Example 3 of the present disclosure.
Figure 3:
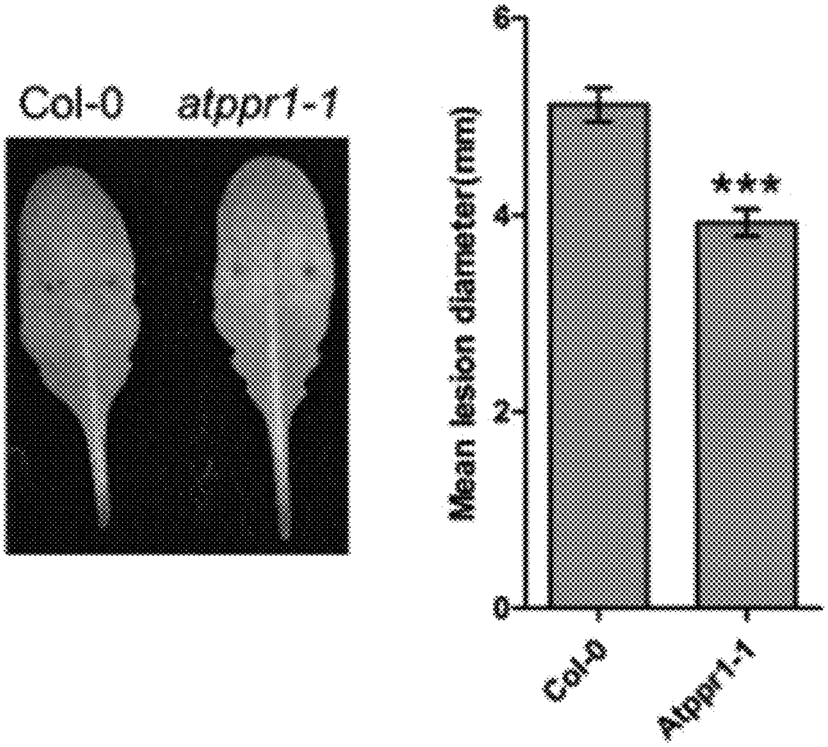
FIG. 3 is a schematic diagram illustrating the resistance of an AtPPR1-knockout mutant of *Arabidopsis thaliana* to *Phytophthora capsici* (P *capsici*) according to Example 3 of the present disclosure.
Figure 4:
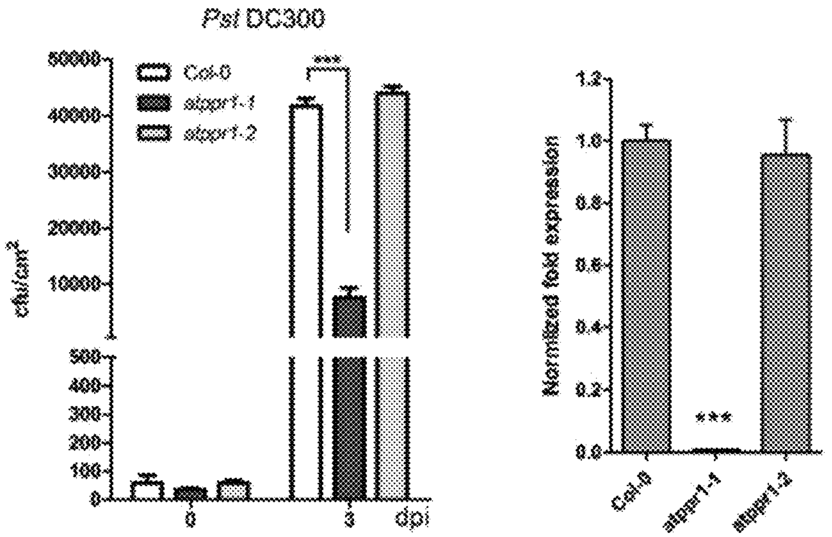
FIG. 4 is a schematic diagram illustrating the resistance of an AtPPR1-knockout mutant of *Arabidopsis thaliana* to *Pseudomonas syringae* (*P. syringae*) according to Example 3 of the present disclosure.

Results are shown in FIG. 2, FIG. 3, and FIG. 4. In FIG. 2, the left panel shows the observation results of lesions about 2 days after inoculation with the zoospores of *P. parasitica*, and the right panel shows the evaluation results of disease degree. In FIG. 3, the left panel shows the observation results of lesions about 46 h after inoculation with the zoospores of *P. parasitica*, and the right panel shows the evaluation results of lesion diameter. In FIG. 4, the left panel shows that the cfu value of *P. syringae* in the atppr1-1 mutant is significantly smaller than that in the wild-type *Arabidopsis thaliana* three days after the inoculation, and the right panel shows the expression levels of AtPPR1 in the two mutants detected by the quantitative PCR technique.

Example 4

This example showed that silencing NbPPR1 in *Nicotiana benthamiana* could improve the resistance to *P. parasitica* and *P. infestans*, including the following steps:

Step 1: An NbPPR1-specific fragment of about 300 bp was selected and inserted at a site between EcoR1 and Xho 1 to construct a pTRV2-NbPPR1 silencing vector; and the NbPPR1-specific fragment had a nucleotide sequence of SEQ ID NO. 1, specifically:

AGCTGAGGCTTTGATGGAAAAAATGTCCGAATGTGGTTTCTTGAAATGCC

CTCTTCCTTATAATCACATGCTATCCTTATACATATCCCAAGGGCAACTA

GAGAAGGTTCCCCGCCTGATTCAGGAATTGAAGAAAAATAGCTCTCCTGA

TATTGTCACATACAACCTGGAGTTGGCAGTTTGTGCATCCCAGAATGATG

TTGAAGCTGCAGAGAAAACATTCGTTGAGCTAAAGAAGGCAAAATTGGAT

CCTGATTGGATAACGTTTAGCACATTAACAAACATCTATATTAAAAGCTC

ACTTCAGGATAAAGCAAAGTC.

Step 2: pTRV1, pTRV2-GFP, and a pTRV2 vector inserted with a target fragment were electroporated into *Agrobacterium tumefaciens*, the *Agrobacterium tumefaciens* infiltration method was used to achieve the joint transient expression of pTRV1-transformed *Agrobacterium tumefaciens* and pTRV-NbPPR1-transformed *Agrobacterium tumefaciens* on *Nicotiana benthamiana*, and generally, the *Nicotiana benthamiana* was injected at a final concentration of $OD_{600}$=0.25.

Step 3: A silenced phytoene desaturase (PDS) gene was adopted as a positive control, and GFP was adopted as a negative control. When the positive control exhibited a significant silencing effect (2 to 3 weeks later), leaves of the experimental group were selected and inoculated with pathogens for analysis, and specific primers were designed to detect the expression of PPR1 in silent plants.

Step 4: About 0.1 g of a *Nicotiana benthamiana* sample was collected to extract RNA, which was reverse-transcribed into cDNA; then specific primers were designed; and the expression of PPR1 was detected using the real-time fluorescent quantitative PCR technology.

Step 5: NbPPR1-silenced *Nicotiana benthamiana* leaves were collected, and GFP-silenced plants were adopted as a control. The leaves were scratched and inoculated with about 2,000 GFP-labeled zoospores of *P. parasitica*, and then cultivated in a 23° C. incubator in the dark for about 40 h. Then a lesion diameter was observed and measured.

Step 6: After fresh *P. infestans* was cultivated for about 10 days, about 5 mL of sterile water was added to the culture to stimulate zoospores at 4° C. for about 1 h to 2 h. After a large number of zoospores were released, about 1,500 zoospores were inoculated at each inoculation site. A lesion diameter was observed and measured after the leaves were cultivated at 16° C. for 5 days. 10 days after the inoculation, leaves were collected, and produced sporangia were counted.

Step 7: The growth and flowering of silent plants were continuously observed 3 to 6 weeks after the injection.

Figure 5:
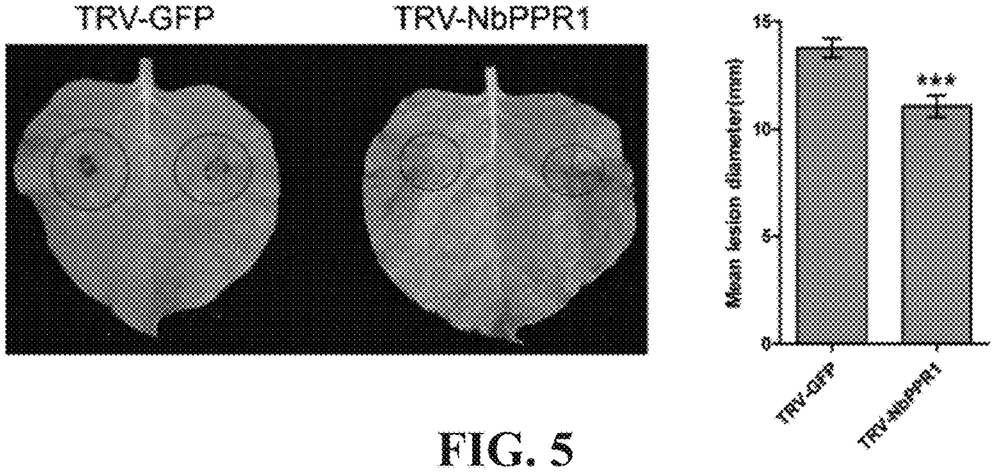
FIG. 5 is a schematic diagram illustrating the result of enhancing the resistance to *P. parasitica* by silencing NbPPR1 in *Nicotiana benthamiana* according to Example 4 of the present disclosure.
Figure 6:
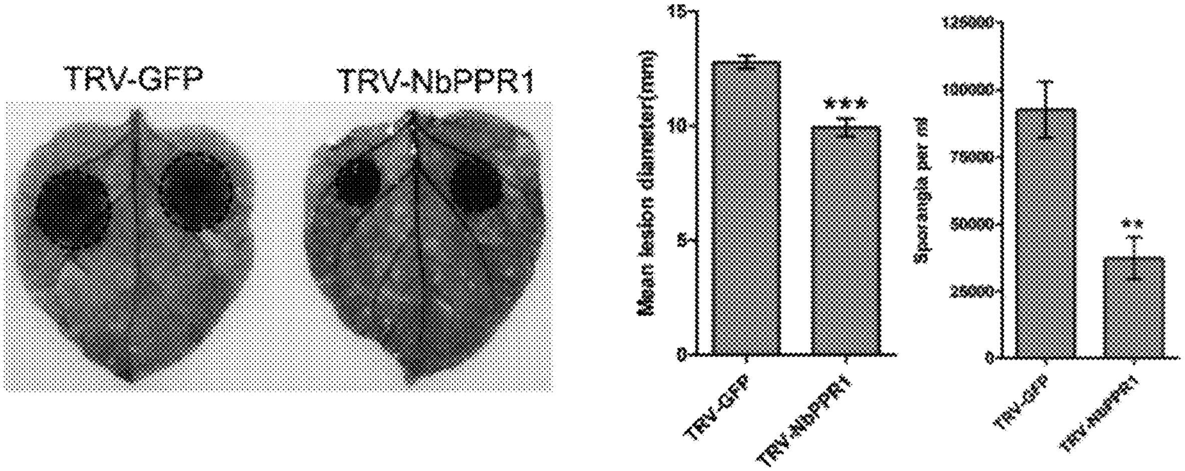
FIG. 6 is a schematic diagram illustrating the result of enhancing the resistance to *P. infestans* by silencing NbPPR1 in *Nicotiana benthamiana* according to Example 4 of the present disclosure.
Figure 7:
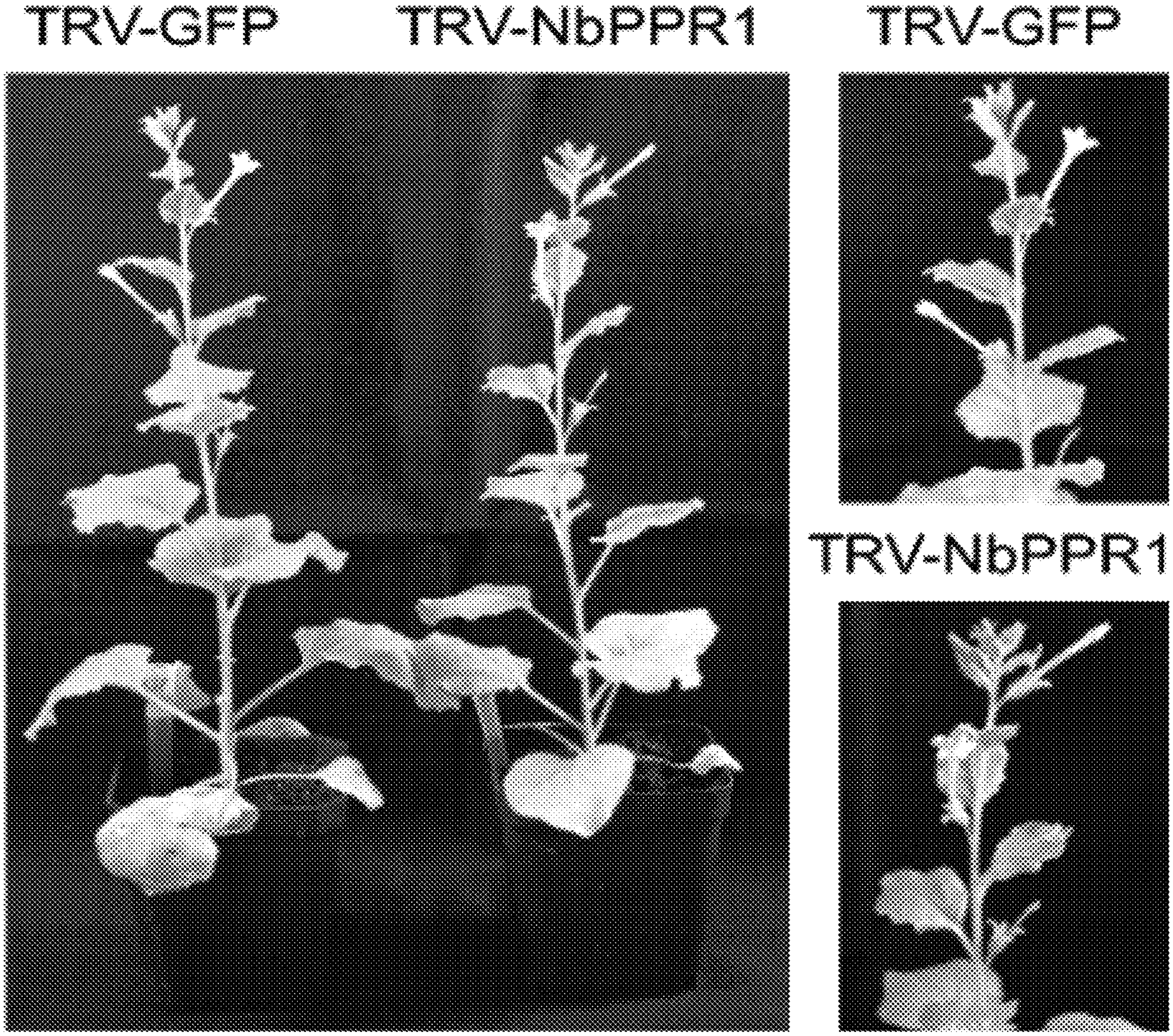
FIG. 7 is a schematic diagram illustrating the growth phenotype of NbPPR1-silent plants according to Example 4 of the present disclosure.

Results are shown in FIG. 5, FIG. 6, and FIG. 7. In FIG. 5, the left panel shows the observation results of lesions about 46 h after inoculation with the zoospores of *P. parasitica*, and the right panel shows the measurement results of lesion diameter. In FIG. 6, the left panel shows the observation results of lesions about 5 days after inoculation with the zoospores of *P. infestans*, the middle panel shows the measurement results of lesion diameter, and the right panel shows the production of sporangia 10 days after inoculation with *P. infestans*.

The AtPPR1 gene of the present disclosure is cloned for the first time as a negative immunoregulatory factor that affects plant ROS and hormone signal transduction. An AtPPR1 gene-overexpressed transgenic *Arabidopsis thaliana* material is constructed through genetic engineering, and the in vitro leaf inoculation experiment proves that AtPPR1-overexpressed *Arabidopsis thaliana* is more susceptible to infection of *P. parasitica*. An AtPPR1 gene-deficient mutant is constructed through genetic engineering, and it is found that the mutant can significantly increase the resistance to pathogens such as *Phytophthora* and *P. syringae*. An NbPPR1-deficient *Nicotiana benthamiana* plant material is obtained through virus-induced gene silencing (VIGS), and it is proved by the in vitro leaf inoculation experiment that this material can enhance the resistance to *P. parasitica* and *P. infestans*. Experimental results prove that the function of the AtPPR1 gene to improve *Phytophthora* resistance of plants can be used for the selective breeding of *Phytophthora*-resistant varieties.

In addition, it is found from the analysis by the real-time fluorescent quantitative PCR technology that the AtPPR1 gene interferes with the signaling pathways of endogenous SA and JA in plants, and it is also found from ROS determination that AtPPR1-deficient plants show stronger ROS. Results show that AtPPR1, as a new negative immunoregulatory factor in plants, negatively regulates the resistance of plants to *Phytophthora* by interfering with downstream signal transduction of endogenous JA and SA and ROS signals in plants.

The above shows and describes the basic principles, main features, and advantages of the present disclosure. It should be understood by those skilled in the art that, the present disclosure is not limited by the above examples, and the above examples and the description only illustrate the principle of the present disclosure. Various changes and modifications may be made to the present disclosure without departing from the spirit and scope of the present disclosure, and such changes and modifications all fall within the claimed scope of the present disclosure. The protection scope of the present disclosure is defined by the appended claims and equivalents thereof.

What is claimed is:

1. A method for improving *Phytophthora* resistance of *Arabidopsis thaliana*, potato, or *Nicotiana benthamiana*, comprising the following steps:

constructing a pentatricopeptide repeat 1 (PPR1)-deficient mutant to reduce an expression level of a protein encoded by an endogenous PPR1 gene of the *Arabidopsis thaliana*, potato, or *Nicotiana benthamiana*, wherein, the endogenous protein encoded by the PPR1 gene has the amino acid sequence of SEQ ID NO: 7 of the *Arabidopsis thaliana*, SEQ ID NO: 10 of the *Nicotiana benthamiana*, SEQ ID NO: 8 or SEQ ID NO: 9 of the potato.

2. The method according to claim 1, wherein, constructing the PPR1 deficient mutant comprises: constructing a *Nicotiana benthamiana* pentatricopeptide repeat 1 (NbPPR1)-deficient *Nicotiana benthamiana* through virus-induced gene silencing (VIGS); or constructing defective potato through VIGS, wherein, an object of the gene silencing is a homologous gene of the PPR1 gene in the sequenced potato genome.

3. The method according to claim 2, wherein, constructing the NbPPR1-deficient *Nicotiana benthamiana* through VIGS comprises the following steps:

1) Inserting an NbPPR1-specific fragment of SEQ ID NO: 1 into a tobacco rattle virus RNA2-based plasmid (pTRV2) to obtain a silencing vector;

2) Transforming a tobacco rattle virus RNA1-based plasmid (pTRV1) and the silencing vector respectively into *Agrobacterium tumefaciens* to obtain a first recombinant *Agrobacterium tumefaciens* and a second recombinant *Agrobacterium tumefaciens*; and 3) Transforming the first recombinant *Agrobacterium tumefaciens* and the second recombinant *Agrobacterium tumefaciens* into *Nicotiana benthamiana* for joint transient expression.

4. The method according to claim 3, wherein, the first recombinant *Agrobacterium tumefaciens* and the second recombinant *Agrobacterium tumefaciens* are transformed into *Nicotiana benthamiana* at a final concentration of $OD_{600}$=0.25.

5. The method according to claim 3, wherein, the step of transforming the first recombinant *Agrobacterium tumefaciens* and the second recombinant *Agrobacterium tumefaciens* into *Nicotiana benthamiana* for joint transient expression comprises an *Agrobacterium tumefaciens* infiltration method.

* * * * *